United States Patent
Shibuya

(10) Patent No.: US 9,589,102 B2
(45) Date of Patent: Mar. 7, 2017

(54) BASE SEQUENCE CLUSTER GENERATING SYSTEM, BASE SEQUENCE CLUSTER GENERATING METHOD, PROGRAM FOR PERFORMING CLUSTER GENERATING METHOD, AND COMPUTER READABLE RECORDING MEDIUM ON WHICH PROGRAM IS RECORDED AND SYSTEM FOR PROVIDING BASE SEQUENCE INFORMATION

(75) Inventor: Tetsuo Shibuya, Yamato (JP)

(73) Assignee: International Business Machines Corporation, Armonk, NY (US)

( * ) Notice: Subject to any disclaimer, the term of this patent is extended or adjusted under 35 U.S.C. 154(b) by 938 days.

(21) Appl. No.: 13/209,097

(22) Filed: Aug. 12, 2011

(65) Prior Publication Data

US 2011/0295977 A1 Dec. 1, 2011

Related U.S. Application Data

(62) Division of application No. 10/426,118, filed on Apr. 29, 2003, now Pat. No. 8,032,305.

(30) Foreign Application Priority Data

May 21, 2002 (JP) .................................. 2002-146201

(51) Int. Cl.
*G01N 33/48* (2006.01)
*G01N 33/50* (2006.01)
(Continued)

(52) U.S. Cl.
CPC .............. *G06F 19/24* (2013.01); *G06F 19/12* (2013.01); *G06F 19/18* (2013.01); *G06F 19/20* (2013.01); *G06F 19/22* (2013.01)

(58) Field of Classification Search
None
See application file for complete search history.

(56) References Cited

U.S. PATENT DOCUMENTS 5,556,749 A * 9/1996 Mitsuhashi et al. ......... 435/6.18
6,519,583 B1 * 2/2003 Koleszar et al. .............. 702/20
(Continued)

FOREIGN PATENT DOCUMENTS

CA 2314447 A1 1/2001

OTHER PUBLICATIONS

Drmanac et al., Sequencing of Megabase Plus DNA by Hybridization: Theory of the Method, Genomics 4:114-128 (1989).
(Continued)

*Primary Examiner* — Russell S Negin
(74) *Attorney, Agent, or Firm* — Karen Canaan; CanaanLaw, P.C.

(57) ABSTRACT

Provided is a base sequence cluster generating system, method, and program product for performing cluster generation. The base sequence cluster generating system utilizes a computer system having a database containing base sequences receives a query sequence over. The computer uses spliced base sequences as a query sequence to generate a first cluster including base sequences that are likely to constitute a spliced pair with the query sequence. Spliced alignment is applied to the generated first cluster to generate a second cluster including spliced pairs. The generated second cluster is returned to the requester.

19 Claims, 16 Drawing Sheets

(51) Int. Cl.
*G06F 19/24* (2011.01)
*G06F 19/18* (2011.01)
*G06F 19/20* (2011.01)
*G06F 19/12* (2011.01)
*G06F 19/22* (2011.01)

(56) References Cited

U.S. PATENT DOCUMENTS

| | | | |
|---|---|---|---|
| 6,893,840 B2 | 5/2005 | Thudium et al. | |
| 7,702,595 B2* | 4/2010 | Shibuya | 706/13 |
| 7,856,409 B2* | 12/2010 | Shibuya | 706/13 |
| 7,877,336 B2* | 1/2011 | Shibuya | 706/13 |

OTHER PUBLICATIONS

Florea et al., A Computer Program for Aligning a cDNA Sequence with Genomic DNA Sequence, Genome Research 8:967-974 (1998).
Kawai et al., Functional Annotation of a Full-Length Mouse cDNA Collection, Nature 409:685-690 (2001).
Lewin, Genes V, Oxford University Press, New York, 1994, pp. 150 and 164.
Mott, Est_Genome: A Program to Align Spliced DNA Sequences, Cabios 13(4):477-478 (1997).
Navarro, A Guided Tour to Approximate String Matching, ACM Computer Surveys 33(1):31-88 (2001).
Navarro and Baeza-Yates, A New Indexing Method for Approximate String Matching, Proc CPM99 LCNS 1645:163-185 (1999).
Saris et al., cDNA Sequence and Tissue Distribution of the mRNA for Bovine and Murine p11, the S100-Related Light Chain of the Protein-Tyrosine Kinase Substrate p36 (Calpactin I), The Journal of Biological Chemistry 262:10663-10671 (1987).
Shibuya et al., Accurate cDNA Clustering Algorithm Based on Spliced Sequence Alignment, Technical Report of IEICE COMP2002-11 (May 2002).
Shibuya et al., Efficient Filtering Methods for Clustering cDNAs with Spliced Sequence Alignment, Bioinformatics 20(1):29-39 (2004).
Tanaka et al., Autonomous Distributed Genome Database and its Application to Mouse cDNA and Human Genome Sequence Matching, Genome Informatics 11:378-379 (2000).
Usuka et al., Optimal Spliced Alignment of Homologous cDNA to a Genomic DNA Template, Bioinformatics 16 (3):203-211 (2000).
Zhang et al., Fission Yeast Gene Structure and Recognition, Nucleic Acids Research 22:1750-1759 (1994).

* cited by examiner

```
for (i=0;i<=k;i++) positions[i] = 0;
min_k = 0;
for (child_position=1; child_position<=m; child_position++){
    max_k = min {k, child_position};
    //    If min_k<=i<= max_k and
    //    position[i] is less than or equal to m,
    //    one of subsequences of
    //    P[1..positions[i]] has an edit distance
    //    of i to C[1..child_position].
    //    min_k indicates the least possible number of mismatches
    //    max_k indicates the largest possible number of mismatches
    for (i=max_k; i>min_k ;i--) {
        positions[i] = min { next_char_position(P, positions[i]+1, C[child_position]),
                             positions[i-1] };
        if (positions[i] > m) {
            min_k = i+1;
        }
    }
    if (min_k > k) {
①       The spliced edit distance of this set is greater than k, therefore
        it may not be a splicing pair.
    }
}
→ ② The spliced edit distance of this set is equal to min_k, therefore it is
     likely to be a splicing pair.
```

FIG. 6

| child_position | 1 | 2 | 3 | 4 | 5 | 6 | 7 | 8 |
|---|---|---|---|---|---|---|---|---|
| positions[s] | 2 | 3 | 5 | 11 | - | - | - | - |
| positions[1] | 0 | 1 | 3 | 5 | 6 | 7 | 8 | 11 |
| positions[2] | - | 0 | 1 | 3 | 5 | 6 | 7 | 8 |
| positions[3] | - | - | 0 | 1 | 3 | 5 | 6 | 7 |
| min_k | 0 | 0 | 0 | 1 | 1 | 1 | 1 | 3 |
| max_k | 1 | 2 | 3 | 3 | 3 | 3 | 3 | 4 |

```
for (j=0;j<nj;j++) {
    N0,j = child_external_gap_penalty × j;
}
for (i=0;i<m;i++) {
    Ni,0 = parent_external_gap_penalty × i;
}
for (j=1;j<nj;j++) {
    for (i=1; K=m; i++) {
        If (i<m) child_gap_score = child_internal_gap_score;
        else child_gap_score = child_external_gap_score;
        If (j<n) parent_gap_score = parent_internal_gap_score;
        else parent_gap_score = parent_external_gap_score
        Nij = min { Nij-1 + child_gap_score,
                    Ni-1j + parent_gap_score,
                    Ni-1j-1 + match(C[i],P[j]),
                    Sij-min_splice_length + acceptor(Pj) };
        Sij = min { Nij + donor(Pj), Sij-1);
    }
}
Score is Nnm.
```

FIG. 12

```
GGCTCTTGAACAAAACGCTGGAGCTGAGGATTTCATCTCGGATTTCATCTAACATTATGGGCCGCAAGAAAGTTGCTCGCG      80
GGCTCTTGAAAAAACGCTGGAGCTGAGGATTCATCTCGGATTTCATCTAACATTATGGGCCGCAAGAAAGTTGCTTGCG        80
||||||||||||  ||||||||||||||||| |||||||||||||||||||||||||||||||||||||||||||| |||
GATCCAGGAAAGAGAGACGGTCGTGTTCGGCGACCCTCTGGCGCCCTCTGGATGCTTTCGCTGAAGAGGTGGGCGCTGCG     160
GATCCAGGAAAGAGAGACGGGTCGTGTTCGGCGACCCTCTGGCGCCCTCTGGATGCTTTCGCTGAAGAGGTGGGCGCTGCG    160
|||||||||||||||||||| |||||||||||||||||||||||||||||||||||||||||||||||||||||||||||
CTGCGTGGTGAGTTTGGAGCAGTCGGAGCAGTCGGGAGCAGCGGTCGGGCCTGGGAGCAGGAGCGCTGAGGACCCGGCCTTCTCTCTCC      240
CTGCGTG===============================================================================      167
|||||||
TTGTAGCATCCGTGCAGCCCGAGGAGGCCGAGGACCAGGGCGGCCCGGGCCCTGCCTTGTGCGTGCCTGCCTTGCCTTGGCTATG      320
====CATCCGTGCAGCCCGAGGAGGCCGAGGACCAGGGCGGCCCGGGCCCTGCCTTGTGCGTGCCTGCCTTGCCTTGGCTATG        241
    |||||||||||||||||||||||||||||||||||||||||||||||||||||||||||||||||||||||||||||
TGGGAGCTTGGTCACTGCGACCCCAAGGCTGCACGGGCCGCAAACTGGCCCGTCTGGGTCTGGTGCGCTCGGTCCTGCCTGCGCCT      400
TGGGAGCTTGGTCACTGCGACCCCAAGGCTGCACGGGCCGCAAACTGGCCCGTCTGGGTCTGGTGCGCTCGGTCCTGCCTGCGCCT      321
|||||||||||||||||||||||||||||||||||||||||||||||||||||||||||||||||||||||||||||||||
GAGCCAAAGGTTTGGCGGTCTGGTGCTCAGCCCAGTAGGCACTGAGTACGTGTCTCCGGACAGCAGGTAGACACCAGAGG      480
GAGCCAAAGGTTTGGCGGTCTGGTGCTCAGCCCAGTAGGCACTGAGTACGTGTCTCCGGACAGCAGGTAGACACCAGAG==     480
|||||||||||||||||||||||||||||||||||||||||||||||||||||||||||||||||||||||||||||
CCTGGGGATCGGGAGGGGTCGGAGAGGGGTTGGAATGCCCTTCCCACCATCTTGTCTTTGTTAAACTGCCCTGTATCAG      560
===============================================================================      387
GAGTATCATTTTCTTCAAGCCTTGCTTATTGGTCTTGGATGTCCACATCTTCATATGAGCAGAGTTGTATTTAATTTGA     640
==============================================================================      387
CCCTTTTCATAGAGACCAGGCTATAGTGTAGAAAGCCTAGGAGAAGAAACATTTGTTGTGTAAAGTAAACACTGTCCAGCTACC     720
=================================================================================      387
CTCAACTGCTTCCTGAAGGGTTCTTTCTACTATTGCAATAAACCATAACTTGAAATAGCAGAGTGATCTCTCATCTGTA      800
================================================================================      387
GTGAAGCCAGTCTCCAAGGATGTGCCTTATTTGGGCCCTAGAACCTACCCTACACTCTCTGACAGACAGCTGGTGGCAC      880
====================================================ACAGCTGGTGGCAC      387
                                                    ||||||||||||||
AGTCAGGGGTCGCAGTCATAGACTGCTCCTGGGCCAAACTGCTGACGACGACACACCCTTCAGAAGATGCGAGGGAGCCACTTG      960
AGTCAGGGGTCGCAGTCATAGACTGCTCCTGGGCCAAACTGCTGACGACGACACACCCTTCAGAGAGATGCGAGGGAGCCACTTG      481
|||||||||||||||||||||||||||||||||||||||||||||||||||||||||||||||||| |||||||||||||||||
CGGCTCCTGCCTTACCTCGTAGCTCGTAGCTGCCAACCCTGTAAACTATGGCGGCCCTGCAAACTTTCCTGTGTGGAAGCTTTCGC     1040
CGGCTCCTGCCTTACCTCGTAGCTCGTAGCTGCCAACCCTGTAAACTATGGCCGGCCCTGCAAACTTTCCTGTGTGGAAGCTTTCGC     1040
|||||||||||||||||||||||||||||||||||||||||||||||||||| ||||||||||||||||||||||||||||||||
```

FIG. 16

```
TGCTGCCTTCTGCATCGTAGGCTTTTCAGACCTTGCTGTCATTTGCTTCGGAAGTTTAAGTGGGCAAGGGCTTCCTGG  1120
TGCTGCCTTCTGCATCGTAGGCTTTTCAGACCTTGCTGTCATTTGCTTCGGAAGTTTAAGTGGGCAAGGGCTTCCTGG  641

ACCTGAACCGGGAGCTCCTGGATAAGTACGCAGCTTGCCGTGGCCCGGAGGAGGTGTTGCAGGCTGAACAGGGGTACTTG  1200
ACCTGAACCGGGAGCTCCTGGATAAGTACGCAGCTTGCCGTGGCCCGGAGGAGGTGTTGCAGGCTGAACAGGGGTACTTG  721

GCTAGCACCAGGGACACGCCTGAAGAGGACATCGGTGAGTCCTGGTGTTGGCTGGGAGCCCAGAGAAGCAATCAAGTCC  1280
GCTAGCACCAGGGACACGCCTGAAGAGGACATCG===========================================  755

CTCCAGGGCCTTAGGAGCCTAGAGCCTGAAAATCACTTAGAAGTCCCCTTCCTCTCTTCTTCTTTCTTTCTTTT  1360
============================================================================  755

TTTTGGGGGTGGGGGTGGGGGTGGGGAGAGGGTTTCTGTGTAGTCCTCGGCTGTCCTGGAACTCACTTTGTAGACCAGG  1440
============================================================================  755

CTGGCCTCAAAACTCAGAAATCCGCCTGCCTCTCCCGAGTGCTGGGATTAAAGGTGTGCGCCACCACGCCCTCTCTT  1520
============================================================================  755

TCTGTGTTCAGATCCCTTTGACGTGGACTCAGTGCGGGAGTTTGTGAATCTCAACAGGCCCGTGGCCAGCACCCGGTAC  1600
=========GATCCCTTTGACGTGGACTCAGTGCGGGAGTTTGTGAATCTCAACAGGCCCGTGGCCAGCACCCGGTAC  824

CTGAGGACATGGATGACACTGATGGTCTGAGGAGGAGCACAGTGAAGATTCTGAGGAGGAGGACAGTGAGTGTGAGGAACCA  1680
CTGAGGACATGGATGACACTGATGGTCTGAGGAGGAGCACAGTGAAGATTCTGAGGAGGAGGACAGTGAGTGTGAGGAACCA  984

CACTGAAATTTGGAAAGGGATCAAGAAACGACAAGAGAGAGACTGAAGGTCACAAACATATTATTGAAGCTGGTGTGCATTAT  1840
CACTGAAATTTGGAAAGGGATCAAGAAACGACAAGAGAGAGACTGAAGGTCACAAACATATTATTGAAGCTGGTGTGCATTAT  1064

TCAGAAGTGGCAGTAGGACCTGGGGATGGACGGGCCTGCTGGGACAACCTTGTTTAGTGTCCTGCCTTAGTGCTCTCAAT  1920
TCAGAAGTGGCAGTAGGACCTGGGGATGGACGGGCCTGCTGGGACAACCTTGTTTAGTGTCCTGCCTTAGTGCTCTCAAT  1920

AAAACCAAGGAGACCCC--  1937
AAAACCAAGGAGACCCCT  1162
```

*FIG. 17*

BASE SEQUENCE CLUSTER GENERATING SYSTEM, BASE SEQUENCE CLUSTER GENERATING METHOD, PROGRAM FOR PERFORMING CLUSTER GENERATING METHOD, AND COMPUTER READABLE RECORDING MEDIUM ON WHICH PROGRAM IS RECORDED AND SYSTEM FOR PROVIDING BASE SEQUENCE INFORMATION

CROSS-REFERENCE TO RELATED APPLICATIONS

The instant application is a divisional of U.S. patent application Ser. No. 10/426,118, filed on Apr. 29, 2003, which claims the benefit of JP2002-146201, filed on May 21, 2002, both applications being incorporated herein in their entireties.

REFERENCE TO A SEQUENCE LISTING

The instant application includes a sequence listing in computer readable form (CRF), which is incorporated in its entirety herein.

FIELD OF THE INVENTION

The present invention relates to technology, including methods, systems, and program products for systematizing organism-derived base sequences and more particularly to a cluster generating system that quickly determines whether a given base sequence is derived from another base sequence by splicing (cutting) and generates a cluster, that is, it identifies genes that appear to be expressed as linked groups.

BACKGROUND

Analyzing messenger RNA ("mRNA") expressed in organisms is a very important and useful approach to obtaining various biochemical findings. This is because proteins of eucaryotes are generated by translation of the mRNA. It is known that mRNA, which is transcribed and generated from DNA, is reduced by a process known as splicing, that is, a number of cutting steps, to smaller mRNA before translated into protein. As a result, a plurality of mRNAs may be generated from originally the same gene nucleotide sequence or region by transcription and splicing. Therefore, it can be determined whether or not a gene is expressed in an organism by checking for the presence of only a single base sequence of mRNA derived from the same nucleotide sequence or DNA region. A cDNA library is a database of DNA sequences (hereinafter abbreviated to cDNA) provided by sequencing mRNAs expressed in an organism, reverse-transcribing the resulting mRNA sequences by using a reverse transcriptase to reproduce them as DNA sequences corresponding to the original DNA. The cDNA database reflects the generation process of mRNA and therefore contains a number of cDNAs obtained from mRNAs, which are derived from the same gene region of DNA and have different base chain lengths. Conducting experiments on cDNAs derived from the same regions increases the experiment costs and therefore is often undesirable with the object of determining whether or not appropriate protein is expressed in each particular region in gene regions as described above. Therefore, it is crucially important to accomplish accurate clustering that assembles base sequences obtained from cDNA derived from the same gene region into a single group. This is because such clustering can hasten and efficiently identify tasks for elucidating the function of a particular gene region, reduce experiment costs, and increase search range.

Unfortunately, the above-described clustering involves enormous computational complexity and accordingly it is difficult to obtain significant results within a realistic time period. For example, a method known as spliced alignment has been used to determine whether or not two base sequences constitute a "spliced pair" generated by splicing. This method requires a significant expenditure of computational resources and therefore it is extremely difficult to carry out calculations on all the pairs contained in a typically massive set of sequences such as a cDNA library. A database called FANTOM, which is a mouse cDNA library, contains 21,076 base sequences. It would take more than 100 years for one typical computer to carry out calculations on all of the base sequences in the FANTOM mouse cDNA database. In order to solve the problem, various improvements on the spliced alignment have been considered.

Numerous approaches to improving the efficiency of the above-described clustering have been considered. For example, a Hidden Markov model is used to model a spliced alignment to accomplish alignment in "Optimal Spliced Alignment of Homologous cDNA to a Genomic DNA Template" (Jonathan Usuka, Wei Zhu and Volker Brendel, BIOINFORMATICS Vol. 16, No. 3, 2000, pp. 203-211). Usuka et al. disclose a method for obtaining regions corresponding to cDNA from a text, which is a long sequence (DNA of an organism). According to Usuka et al., particularly, a suffix array is used to select regions that share a 12-mer (a series of 12 bases) in a text array as candidates. It is noted that Usuka et al. do not explain the reason why they used the 12-mer base sequences and do not clarify whether the method can flexibly accommodate variations in chain length of base sequences.

"A New Indexing Method for Approximate String Matching" (G. Navarro and R. Baeza-Yates, Proc. CPM99, LNCS1645, pp. 163-185, 1999) discloses an approximate pattern matching in which an edit distance is defined and partial sequences having an edit distance less than or equal to a predetermined maximum allowable spliced edit distance k are found from a text array. Navarro et al. divide a sequence into d partial sequences, find in the text a partial sequence having an edit distance shorter than each individual partial sequence k/d, and treat it and its surroundings as candidates.

In "EST_GENOME: A Program to Align Spliced DNA Sequences" (R. Mott, CABIOS, Vol. 13, No. 4, 1997, pp. 477-478), a Smith-Waterman dynamic programming algorithm is modified to impose a penalty on splice sites in such a way that splice sites shorter than the minimum allowable length of a splice site are excluded. While various other methods have been proposed, none of them are adequate for clustering base sequences while flexibly accommodating variations in chain length of base sequences with reduced computation time and acceptable amount of hardware resources.

While the prior-art approaches described above disclose clustering approaches, all of them perform the clustering by using criteria (such as conventional similarity) that does not take splicing into consideration and none of them provide a clustering method that takes before-and-after-splicing relation into consideration.

Thus, there is a clear need for a technology that uses spliced alignment to quickly, efficiently, and accurately select candidate base sequences with an adequately high accuracy without omissions before base sequence clustering. Although there are various prior-art approaches as described above, there remains a need for a cluster generating system, a method for enabling base sequence clustering, a program for performing the method, and a computer-readable storage medium containing the program that can associate base sequences held in a database, such as cDNA database, with base sequences that are likely to be generated by splicing from the stored cDNA in order to quickly generate clusters, thereby conserving calculation time and hardware resources. Also, there is a need for a cluster generating system, a method for enabling base sequence clustering, a program for performing the method, and a computer-readable storage medium containing the program that allows a user to generate clusters in a limited time period within reasonable, that is, limited, hardware resource constraints.

In addition, there has been need for a base sequence information system that enables base sequence information relating to spliced pairs to be provided efficiently to a user.

SUMMARY OF THE INVENTION

The method, system, and program product of the present invention meet these needs. The present invention is based on the principle that the time, and computational resources, required for spliced alignments can be considerably reduced if the characteristics of splicing can be used to generate a cluster consisting of base sequences that are likely to constitute a spliced pair before comparison using high-precision, intensive computations such as the spliced alignment. A method of the present invention allows unnecessary base sequences to be excluded by taking before-and-after-splicing relations into consideration and allows a higher-level cluster consisting of base sequences algorithmically selected stringently than the clusters generated by selecting base sequences simply by using hash. A high-precision spliced alignment is applied to the cluster thus obtained, thereby allowing fast and precisely clustering base sequences in before-and-after-splicing relation.

The present invention can be used to filter out a large number of candidates in a cDNA database, for example, before computation and, as a result, computation time can be significantly reduced. Furthermore, the cluster generating method of the present invention can be performed without applying any special process to base sequences. Therefore, results obtained according to the present invention can be provided for the conventional spliced alignment method.

According to the present invention, there is provided a system for generating a cluster of base sequences with respect to splicing, where the splicing generates spliced base sequences from a base sequence. The system comprises: a subsystem for recording the spliced base sequences as a query sequence; a subsystem for comparing a spliced edit distance between the query sequence and the base sequence read from a database with a predetermined maximum acceptable value; and a subsystem for selecting spliced base sequences of which the spliced edit distance between the query sequence and the base sequence is not more than a maximum acceptable value to generate a first cluster and recording the first cluster in a storage subsystem.

According to the present invention, the comparison subsystem preferably comprises a counter decrementing from the maximum acceptable value when a base in the base sequence matches a base in the query sequence. The cluster generating system according to the present invention preferably further comprises a subsystem for generating a second cluster from the first cluster and storing the second cluster in storage subsystem, where the subsystem for generating the second cluster comprises: a subsystem for defining a splice length for the base sequence and generating a score between the query sequence and a base sequence included in the first cluster, the score being weighted according to the splice length; a subsystem for generating a table by repeated generation of the score for the number of times corresponding to the number of bases in the base sequence and the number of bases in the query sequence; and a subsystem for using the table to determine a score for the base sequence with respect to the query sequence.

The splice length according to the present invention is preferably the number of bases within the range from 20 to 60. According to the present invention, the base sequence may include a DNA sequence of a eucaryote and cDNA spliced sequences obtained through reverse transcription from mRNA expressed in the eucaryote or from a base sequence of the mRNA.

The query sequence according to the present invention may include DNA spliced sequences including DNA sequence of a eucaryote and cDNA spliced sequences obtained through reverse transcription from or mRNA expressed in the eucaryote or from a base sequence of the mRNA and cDNA spliced sequences obtained through reverse transcription from mRNA.

According to the present invention, there can be provided a method for generating a cluster of base sequences with respect to splicing, the splicing generating spliced base sequences from a base sequence. The method comprises the steps of: recording the spliced base sequences as a query sequence; comparing a spliced edit distance between the query sequence and the base sequence read from a database with a predetermined maximum acceptable value; and selecting spliced base sequences of which the spliced edit distance between the query sequence and the base sequence is not more than the maximum acceptable value to generate a first cluster and recording the first cluster in storage means.

According to the present invention, there can be provided a computer-readable recording medium on which a program is recorded, the program causing a computer system to perform a method for generating a cluster of base sequences with respect to splicing, the splicing generating spliced base sequences from a base sequence, the program causing the computer system to perform the steps of: recording the spliced base sequences as a query sequence; comparing a spliced edit distance between the query sequence and the base sequence read from a database with a predetermined maximum acceptable value; and generating a first cluster by selecting spliced base sequences where the spliced edit distance between the query sequence and the base sequence is not more than the maximum acceptable value and recording the first cluster in storage.

According to the present invention, there is provided a program for causing a computer system to perform a method for generating a cluster of base sequences with respect to splicing, the splicing generates spliced base sequences from a base sequence. The program causes the computer system to perform the steps of: recording the spliced base sequences as a query sequence; comparing a spliced edit distance between the query sequence and the base sequence read from a database with a predetermined maximum acceptable value; and selecting spliced base sequences of which the spliced edit distance between the query sequence and the base sequence is not more than the maximum acceptable value to generate a first cluster and recording the first cluster in storage means.

According to the present invention, there can be provided a base sequence information providing system for providing information about a cluster of base sequences with respect to splicing, the splicing generating spliced base sequences from a base sequence, the system comprising: a server connected to a network for receiving a query sequence over the network; and a database containing base sequences. The server comprises: a subsystem for recording the spliced base sequences as a query sequence; a subsystem for comparing a spliced edit distance between the query sequence and the base sequence read from a database with a predetermined maximum acceptable value; a subsystem for selecting spliced base sequences of which the spliced edit distance between the query sequence and the base sequence is not more than the maximum acceptable value to generate a first cluster and recording the first cluster in storage; a subsystem for generating a second cluster from the first cluster and storing the second cluster in storage means; and a subsystem for sending the second cluster over the network. It is to be understood that while the above description is with respect to a networked client-server system, the invention maybe implemented on a single computer platform, or with multiple servers.

BRIEF DESCRIPTION OF THE FIGURES

The method, system, and program product of the invention is illustrated in the Figures appended hereto.

FIG. 6 shows a rough pseudo code of the flowchart shown in FIG. 3;

FIG. 12 shows a rough pseudo code for generating a second cluster according to the present invention;

FIG. 16 shows base sequences of SEQ ID NO: 1 (bottom line) and SEQ ID NO: 2 (top line), which are used in an example of the present invention; and FIG. 17 shows base sequences of SEQ ID NO: 1 (bottom line) and SEQ ID NO: 2 (top line), which are used in the example of the present invention (continued from FIG. 16).

DETAILED DESCRIPTION OF THE INVENTION

While the present invention will be detailed below with respect to embodiments shown in the accompanying drawings, the present invention is not limited to the embodiments described below. While the term "splicing" as used herein refers to a mechanism in eucaryotes (and archaebacteria) in certain embodiments, the splicing can be applied to base sequences derived from organisms in general that are generated by a process in which mRNA is spliced to generate shorter base sequences. Focusing on two base sequences, a parent sequence is defined herein as a base sequence before splicing and a child sequence is defined as the base sequence after splicing. A spliced pair is defined as a pair having the interrelation described above.

It is known that there can be a plurality of splicings for a given mRNA and, consequently, the number of types of protein generated in vivo is far larger than the number of genes. Splicing occurs in a region between a site known as a donor site and a site known as an acceptor site in a base sequence. Each of donor and acceptor sites has a distinctive sequence. It is known that, in particular, donor sites almost always start with GT and acceptor sites almost always end with AG. The present invention, however, can also be applied to a pair of sites having similar characteristics.

It is also known that there is a distinctive sequence within a site to be cut (a splice site). There is a lower limit to the length of a splice site. The length of a splice site base is at least approximately 20 to 60 and more often approximately 50 to 60.

The term "alignment" as used herein refers to a method in which a gap (often indicated by "-") is inserted between two or more base sequences as appropriate to arrange them in a line for comparing them with each other.

Essentially, the present invention gives scores to base sequences according to their degree of matching and arranges them in such a manner that the scores become or approximate to the lowest or highest and then the base sequences are compared with each other.

The term "projection" as used herein means that a query sequence is compared with a base sequence that is aligned with a base sequence of interest with an appropriate gap between them and a score is given to the base sequence of interest as described above.

Figure 1:
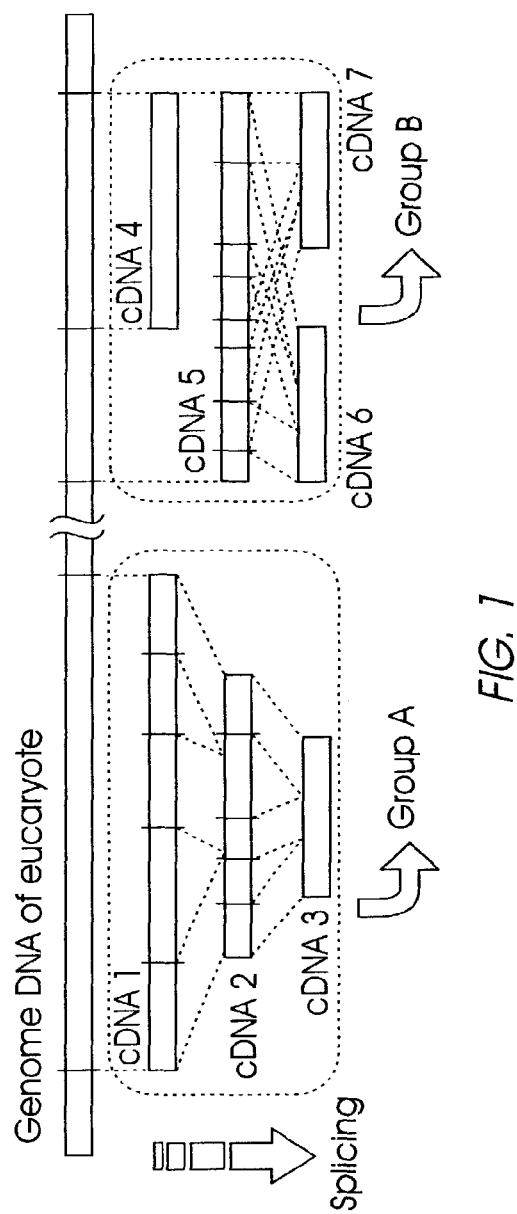
FIG. 1 shows a configuration of a base sequence database to which the present invention is applied.

FIG. 1 schematically shows a configuration of a database containing base sequences to which the present invention is applied. Shown in FIG. 1 are seven cDNA sequences cDNA 1-cDNA 7. In FIG. 1, cDNA 1 and cDNA 5 belong to group A and group B, respectively, and are derived from different DNA regions in genome DNA of a eucaryote. cDNA 2 and cDNA 3 are cDNA generated by reverse transcription from mRNA generated by splicing mRNA corresponds to cDNA 1. cDNA 6 and cDNA 7 are cDNA generated by reverse transcription from mRNA generated by splicing mRNA corresponding to cDNA 5, which is generated by reverse transcription from its corresponding mRNA. They are a spliced pair. Therefore, in order to perform the above-described clustering properly, accurate determination is required as to whether or not sequences are in before-and-after-splicing relation, that is, whether they are a spliced pair.

According to the present invention, cluster generation is accomplished by taking advantage of a non-zero, but very low, probability that a base will change during transcription from DNA to mRNA or in a stage in which mRNA is cut by splicing into short-chained base sequences. A read error can occur during sequencing mRNAs by means of a sequencer. The error rate depends on methods used. For example, it may be approximately 5% or less when draft sequencing, which may have the highest error rate, is used.

The inventor has conducted a close study and found that highly efficient cluster generation can be achieved by defining an error rate r which is a combined rate of changes in bases and sequencing errors and performing cluster generation with the recognition that the mX(1−r) or more bases among m bases in a child sequence (having a length of m) should exist in its parent sequence (having a length of n) without the order in which they appear being changed.

That is, because a child sequence is a subsequence of its parent sequence, the edit distance corresponding to the difference in base sequence between the parent sequence and the child sequence must be less than or equal to m□r. Here, the term "subsequence" of a given base sequence refers to a base sequence provided by omitting some of bases in a base sequence of interest and arranging the remaining bases without changing their order. An edit distance in the present invention is equivalent to the number of operations such as alteration, addition, and deletion of bases that are required to transform a given sequence to another sequence, more particularly, the number of different bases, excluding gaps. In the present invention, deletion is not required to be taken into consideration because only a subsequence of a parent sequence is required to be considered. The term "subsequence" as used herein refers to a base sequence shortened by removing some of bases from a sequence. For example, a base sequence ATCTGG is a subsequence of a base sequence ATGCTAGG.

According to the present invention, a spliced edit distance between a given subsequence of a parent sequence and a child sequence is defined. Variable k is defined as an integer less than or equal to mXr. It is known that the above-described error rate r is well small. Therefore k is expected to be small. According to the present invention, variable k is selected as the maximum acceptable value of the spliced edit distance in cluster generation. Thus, according to the present invention, a cluster can be generated in a computation time of order 0(k+m+n), which is shorter than precise spliced alignment. A memory required for this computation is of order 0(k+n+m). The present invention allows the number of spliced pair candidates to be significantly reduced by using the results of this computation.

Figure 2:
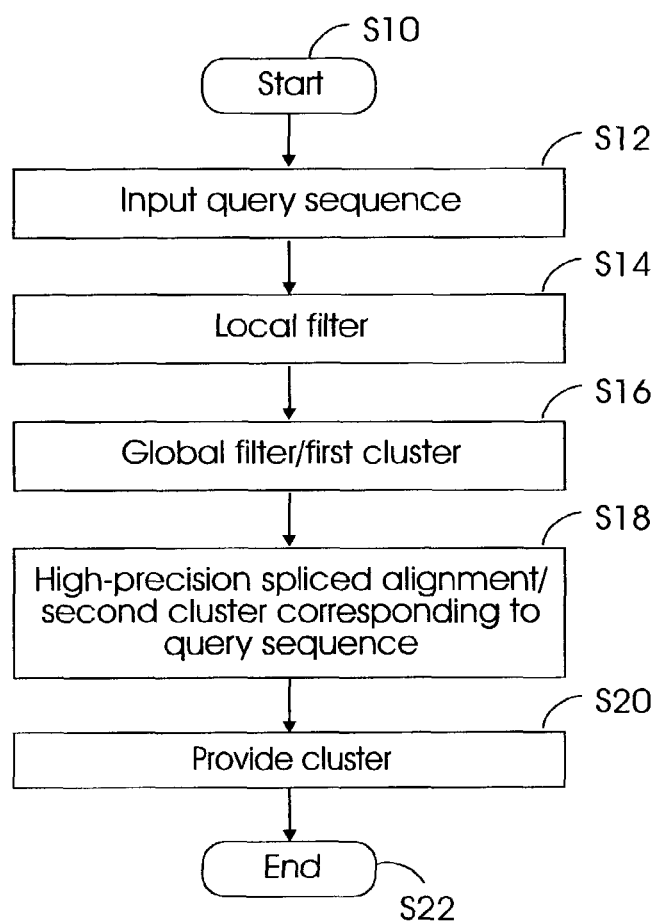
FIG. 2 shows an outline flowchart of a cluster generating method according to the present invention.

FIG. 2 shows a flowchart of a process for generating a cluster of spliced pairs by using a splicing alignment method of the present invention. The clustering method of the present invention starts at step S10. At step S12, a query sequence is set. The query sequence may be directly input through input means such as a keyboard into a computer system that performs cluster generation. Also, the query sequence may be input into the computer system from a client computer over a network. It may be also possible that only authorized users are allowed to input the query sequence by using browser software over a network such as the Internet. The input query sequence is recorded in appropriate buffer memory included in the computer system and called by a central processing unit (CPU) when required to be used for projection of a base sequence in a database.

In the cluster generating method of the present invention, a filter, e.g., an existing filter, that extracts a pair having a common part with consideration given to only base sequences is used to narrow down candidate base sequences at step S14. This filtering may be accomplished by a known method, such as hashing, based on determination whether or not a base sequence includes a base included in the query sequence. A possible embodiment of the present invention does not necessarily require the filtering at step S14.

At step S16 the clustering method of the present invention is caused to be executed to further narrow down candidate spliced pairs. At step S18, high-precision splicing alignment is performed using a first cluster consisting of base sequences that are selected as being likely to be spliced pairs according to the present invention as the population to be subjected to projection to search for an exact spliced pair for the query sequence input by the user, and it is recorded as a cluster.

Then, the cluster obtained at step S18 is presented to the user at step S20 and the method of the present invention ends at step S22. The cluster base sequence may be presented to the user over a network such as the Internet or a local area network (LAN) built using Ethernet®. In a standalone system, which does not use a network, it can be provided to the user by displaying it on a display screen, outputting it on a hardcopy printer, or recording in permanent non-volatile memory, as a magnetic disc drive, or on portable recording means such as a flexible disk, flash memory, and magneto-optical disk.

The user can use the provided cluster information to quickly obtain findings about the spliced pairs recorded in a base sequence database and determine whether or not they are base sequences expressed from the same region of the original chromosome DNA sequence.

Figure 3:
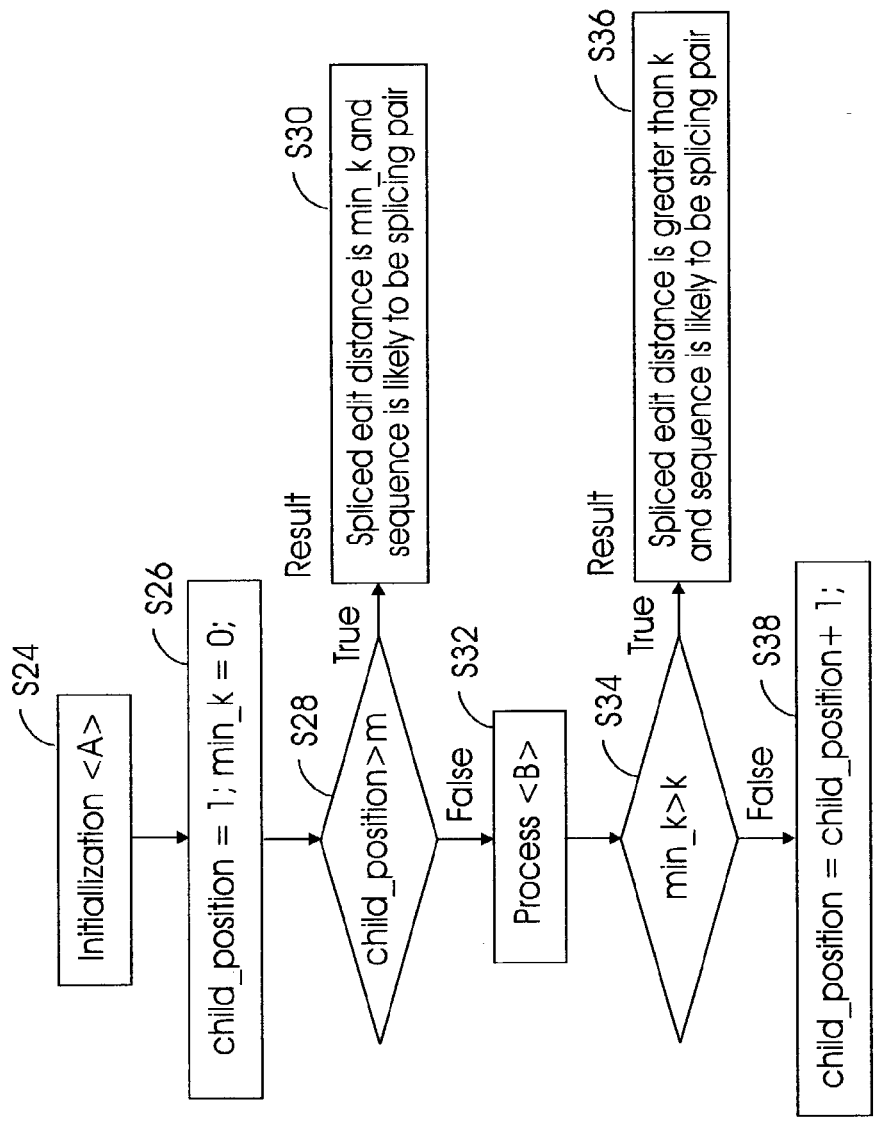
FIG. 3 shows a flowchart of a method for generating a first cluster according to the present invention.

FIG. 3 shows a high level flowchart of a method for generating a first base sequence cluster according to the present invention. The first cluster generating method of the present invention shown in FIG. 3 starts with initialization at step S24. A variable, child_position, is set to 1 to declare that the calculation should start with the starting base of a child sequence and, at the same time, the minimum spliced edit distance, min_k, is initialized at step S26. The minimum spliced edit distance, min_k, is an essential parameter used in the present invention to define the lower limit of the mismatch between bases. It is determined at step S28 whether or not the child_position indicating the position of a base in the child sequence has exceeded m. If the determination has been completed for the bases in the child sequence (true), the number of mismatching bases in the child sequence is less than or equal to the set maximum allowable edit distance k. Therefore, the child sequence of interest is likely to be a spliced pair and is selected as a first cluster. It is recorded in storage, such as a memory or a hard disk at step S30. The determination at step S28 in FIG. 3 is possible because the process in FIG. 3 branches to the determination at step S28 only if the minimum spliced edit distance min_k is always less than the set maximum allowable spliced edit distance, as will be described later.

If the determination at step S28 is negative (false), then the process of the present invention proceeds to step S32, where a process for determining mismatching found in the child sequence is performed, as will be described later. After the completion of the process at step S32, it is determined at step S34 whether the minimum spliced edit distance min_k is greater than the set maximum acceptable value k. If the determination at step S34 is positive (true), then it is not determined to be a spliced pair, is not recorded as the first cluster at step S36, and is not used in the subsequent calculations. Various known methods for excluding the sequence may be used, such as setting an exclusion flag or deleting it from the memory in use. If the determination at step S34 is negative (false), then the base position in the child sequence is incremented at step S38. Then the process branches to step S28 and steps S28 to S38 are repeated to generate the first cluster of child sequences that are likely to be a spliced pair. According to the present invention, clusters that are likely to be child sequences are recorded by using various known methods. For example, child sequence data may be sequentially stored in an area reserved for it in storage means such as a memory or hard disk. According to the present invention, a pair flag may be provided for indicating that a base sequence is to be recorded as a spliced pair and stored in the storage means as data including a base sequence ID and pair flag.

Figure 4:
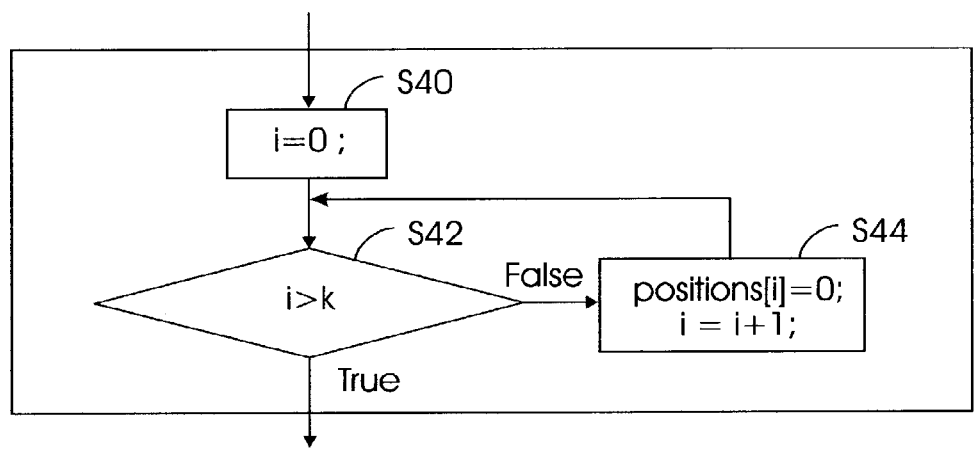
FIG. 4 is a flowchart showing the details of the initialization step shown in FIG. 3.

FIG. 4 is a flowchart showing the initialization at step S24 in detail. As shown in FIG. 4, the initialization according to the present invention first initializes the position i of a base to be subjected to determination in a child sequence at step S40. Then, it is determined at step S42 whether the number of base sequences in the child sequence is greater than the set maximum acceptable value k. If i>k (true), then the initialization ends and the result is returned to step S26 in FIG. 3. If it is determined at step S42 that i is less than or equal to k (false), then a variable, positions[i], is initialized to 0 at step S44, i is incremented. The initialization of variable positions[i] is repeated until determination at step S42 becomes true (i>k).

Figure 5:
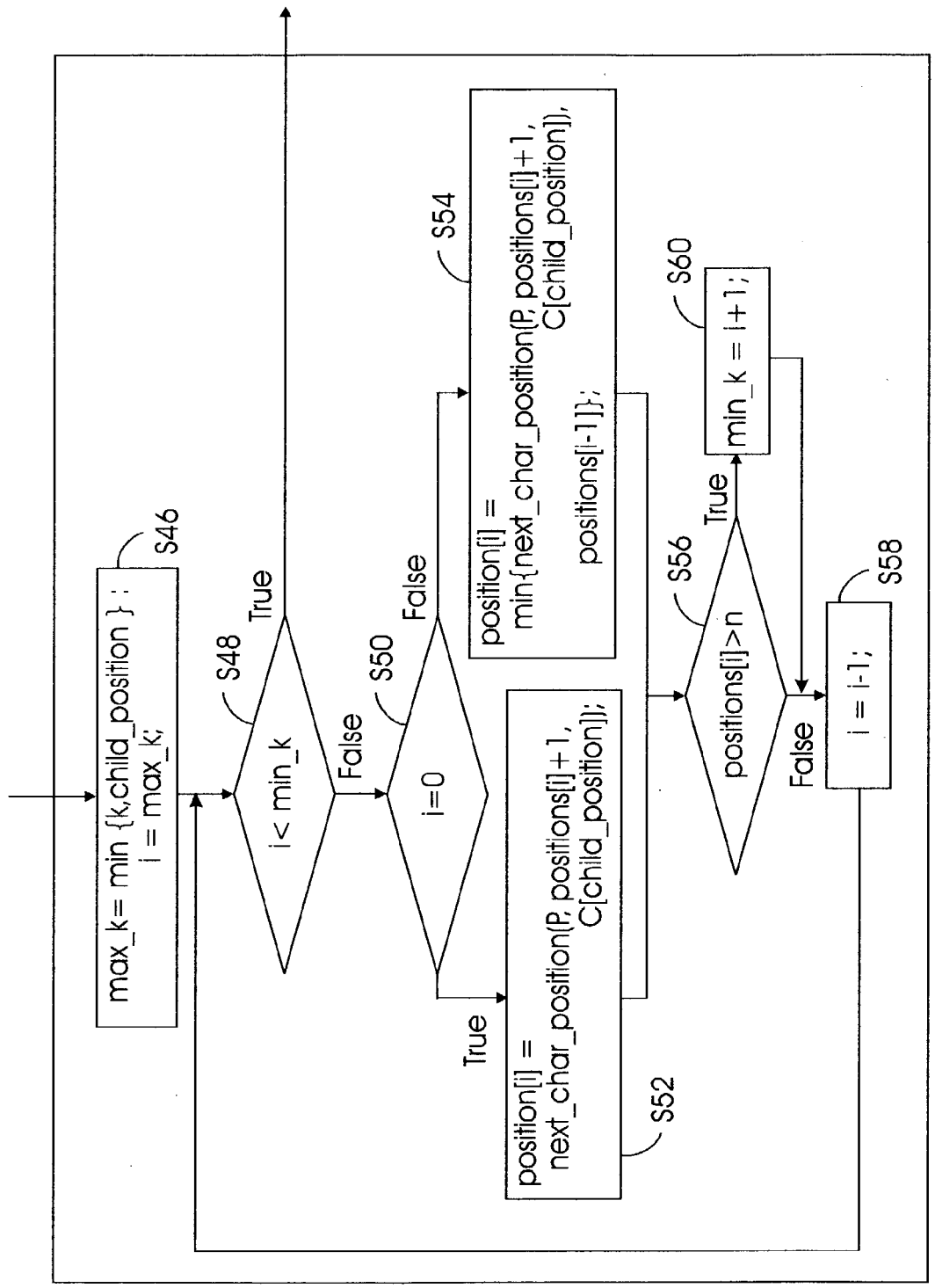
FIG. 5 is a flowchart showing the details of step S32 in the flowchart shown in FIG. 3.

FIG. 5 is a flowchart showing in detail the process at step S32 in the flowchart shown in FIG. 3. At step S46 in the process in FIG. 5, a variable, max_k, is set to the maximum acceptable value k of the spliced edit distance (a positive integer less than or equal to mXr) or a value corresponding to the position of a base of interest in the child sequence, and at the same time, a difference counter i is defined and set to the initial value max_k. The difference counter i starts with the set maximum acceptable value k and is decremented when a match base is found. It is determined at step S48 whether the difference counter i is less than min_k.

As described above, min_k is a variable corresponding to the minimum spliced edit distance in a base between a parent sequence and a child sequence. While the initial value is 0 in the specific embodiment shown at step S26 in FIG. 3, a value other than 0 may be specified by a user as appropriate in consideration of base sequences of interest according to the present invention. If it is determined at step S48 that the difference counter i is less than min_k (true), then the matching determination process is ended by returning the result to step S34 in FIG. 3. On the other hand, if it is determined at step S48 that the difference counter i is greater than or equal to min_k, then it is determined at step S48 whether or not the value of the difference counter i is 0. If i=0 (true), variable position[i] is set to a position in which a base of the child sequence indicated by C[child_position] appears for the first time in its parent sequence P[1, . . . , position[i]+1] at step S52. On the other hand, if i is not 0 (false), determination is made at step S54 as to the next base position in the parent sequence. The value of the previous position[i−1] or the value of the next base position in the parent sequence, whichever is smaller, is set as the value of position[i].

After steps S52 and S54, it is determined whether or not the variable positions[i] updated at step S56 is greater than the number n of bases in the parent sequence of interest. If the variable position[i] is less than or equal to the number n of bases in the parent sequence of interest (false), the value corresponding to a relevant base in the child sequence has been returned. Therefore, it is determined that the parent sequence is likely to constitute a spliced pair with the child sequence of interest, the difference counter i is decremented at step S58 and again determination at step S48 is made. This process is repeated until the condition i<min_k is met. On the other hand, if it is determined at step S56 that the variable position[i] is greater than the number n of bases in the parent sequence of interest (true), then a base of interest in the child sequence has not yet found. If the child sequence were selected as a spliced pair, the risk of causing erroneous determination would increase. Therefore the minimum spliced edit distance min_k is set to i+1 at step S60.

Furthermore, the difference counter i is decremented at step S58 to ensure that determination at step S48 is ended while minimizing the risk, thereby efficiently avoiding unnecessary calculations to improve processing speed. In addition, the above-described process in the present invention effectively uses the characteristics of splicing, rather than using only common bases, to select and extract base sequences that have smaller difference in base sequence than those extracted by using an edit distance, which is set based on the probability of occurrence of errors. As a result, the number of bases extracted can be reduced and the reliability of spliced pairs can be further improved.

According to the present invention, bases such as adenine (A), guanine (G), cytosine (C), and thymine (T) in a base sequence may be compared with those in another base sequence on a character basis or may be compared on a numeric value basis by digitizing the base sequences correspondingly to the four types of bases.

FIG. 6 shows a pseudo code for causing a computer to execute the process shown in the flowchart described above for generating the first cluster. In the pseudo code shown in FIG. 6, a parent sequence is represented by P[1 . . . n] and a child sequence is represented by C[1 . . . m]. A function represented by next_char_position(P, i, c) in the pseudo code shown in FIG. 5 returns the position (integer) of the first base "c" that appears in P[i . . . n]. If no such base exists, it returns n+1. This can be calculated in a acceptable time by generating an appropriate data structure beforehand because the number of types of bases in DNA is limited.

Figures 7, 8:
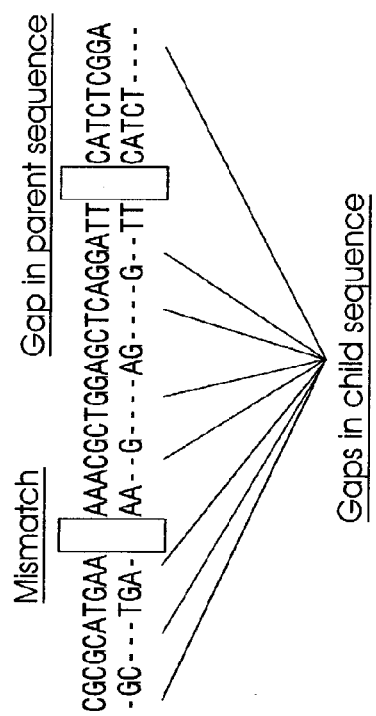
FIG. 7 shows exemplary base sequences of SEQ ID NO: 3 (top line) and SEQ ID NO: 4 (bottom line) to which the present invention is applied.
FIG. 8 shows variables provided in each of repetitive steps of the cluster generating method shown in FIG. 3.

FIG. 7 schematically shows base sequences to be clustered in a process according to the present invention. The minimum approximate parameter is equivalent to alignment shown in FIG. 7 in which gaps in a child sequence are not adversely treated. Suppose that scores are given according to the degree of matching between base sequences as follows: 0 for a match, 1 for a mismatch, 1 for a gap in a parent sequence, and 0 for a gap in a child sequence, for example. Then the minimum alignment score would be equal to the approximate parameter obtained in the pseudo code shown in FIG. 6. The alignment in the embodiment shown in FIG. 7 is the alignment having the minimum score of 2 according to this rating, which equals min_k=2.

The present invention will be described below with respect to the base sequences shown in FIG. 7 with reference to the pseudo code shown in FIG. 6. Because in the embodiment shown in FIG. 7 the parent sequence is "GGCTCTTGAACAAACGCTGGAGCTGAGGAT-TCATCTCGGA" [SEQ ID NO: 3] and the child sequence is "GCTGAGAAGAGGTTTCATCT" [SEQ ID NO: 4], if k□2 is ultimately set, the computation in the process shown in FIGS. 3 to 5 proceeds to the step indicated by reference numeral (2) in the pseudo code and value min_k=2 is obtained, which indicates that they are likely to be a spliced pair.

If k=1 is set in the pseudo code shown in FIG. 6, the clustering process will end at the step indicated by reference numeral (1) and the result is returned that they are unlikely to be a spliced pair. As described above, the sequences that cause the process at step (1) are not examined further. Consequently, the present invention can significantly reduce calculation time.

FIG. 8 is a table showing a specific process of the above-described clustering by using specific parent sequence model and child sequence model that have a shorter base chain length. In FIG. 8, the parent sequence is "CGCGCATGAA" and the child sequence is "GCCCATGC" and it is determined whether or not the edit distance of the two base sequences is less than or equal to k=3. In order to indicate changes in values of child_position, positions[i], min_k, and max_k immediately after process <B> shown in FIGS. 3 to 5, output values are shown in each column in FIG. 8. For the two base sequences shown in FIG. 8, process <B> is called eight times in total. In this case, min_k=2 is output. Thus, it can be found that they are likely to be spliced pair.

In the example shown in FIG. 8, if k=0 (the bases are perfectly matched with each other), then min_k>0 after process <B> on child_position=4. Thus, it can also be seen from FIG. 8 that they are not a spliced pair having a desired degree of approximation between them. A bar "-" in FIG. 8 indicates an entry of position[i] that has not been processed in process <B>.

A process for using precise spliced alignment in the present invention to determine whether sequences are an exact spliced pair will be described below. The precise spliced alignment is performed by using the first cluster generated as described above. Because child sequences whose degree of base sequence matching is such that the number of mismatch bases is within a range desired by a user are selected and contained in the first cluster as described above, the number of base sequences in the first cluster can be limited more strictly than a case where the number of child sequences is limited by clustering that gives consideration only to the types of bases. As a result, the first cluster is composed of base sequences that are highly likely to be spliced pairs. Therefore, the efficiency of the high-precision spliced alignment according to the present invention, which will be described later, can be improved. In the spliced alignment of the present invention, an alignment that provides the lowest score, which will be described below, is obtained from among possible alignments between a parent sequence and a child sequence.

Score=sum{matching score}  [Equation 1]

where
{matching score}=
the number of internal gaps in parent sequence X parent_internal_gap_score+
the number of external gaps in parent sequence X parent_external_gap_score+
the number of internal gaps in child sequence X child_internal_gap_score+
the number of external gaps in child sequence X child_external_gap_score+
the number of splice sites (shortest length: min_splice_length) X splice score+
sum {score of donor site}+sum {score of acceptor site}

A matching score described above, Equation 1, in the present invention can be obtained as follows. A score is assigned to matching between bases beforehand. If they are adjacent to each other, the assigned score is given to that pair. The term "splice site" as used herein refers to a gap that has a length longer than or equal to a splice length (min_splice_length) in a child sequence. As described earlier, its first base part is called a donor site and the last base part is called an acceptor site. An appropriate score is assigned to each of them according to whether it has a characteristic sequence (most of them begin with GT and end with AG). In particular, no score is given to a splice site that begins with GT, for example. That is, the fact that the splice site is contained in is treated advantageously, but a score of 1 is given to other splice sites to treat these unadvantageous.

The term "internal gap" as used herein refers to a gap placed in any position between the first base of a sequence and the last base of the sequence. The term "external gap" as used herein refers to a gap that is placed before the first character of a sequence or after the last character of the sequence.

Figure 9:
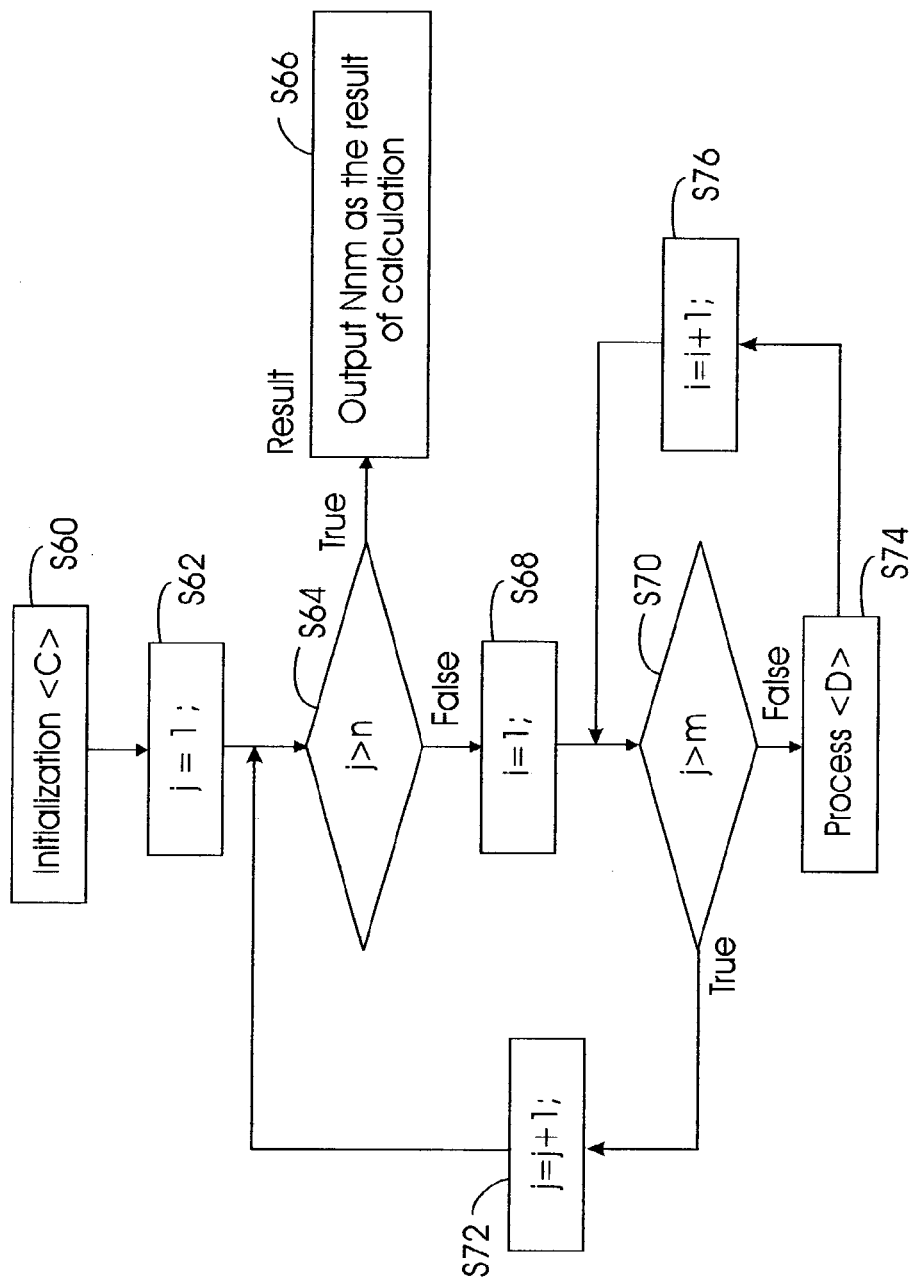
FIG. 9 shows an outline flowchart of spliced alignment according to the present invention.

FIG. 9 shows a flowchart of a process for obtaining the score of alignment under the conditions described above. As shown in FIG. 9, the process for obtaining the score of alignment starts with initialization at step S60. At step S62, a variable j (positive integer) is initialized to 1. Then, j is compared with n at step S64. If j exceeds n (true), the scores of all base sequences have been obtained. Therefore, the result is output as Nmn at step S66. If it is determined at step S64 that j is less than n (false), i is set to 1 at step S68 and i is compared with m at step S70. If the comparison at step S70 shows that the i is greater than m (true), the score of the child sequence is not required to be calculated. Therefore, j is incremented at step S72 and the process branches to step S64. Then determination steps S64 to S70 are repeated to avoid unnecessary calculations. If it is determined at step S70 that i is less than or equal to m (false), the process proceeds to step S74, where the score of each element is calculated. After the completion of the calculation at step S74, i is incremented at step S76 and the above-described process is repeated for i that is less than or equal to m.

Figure 10:
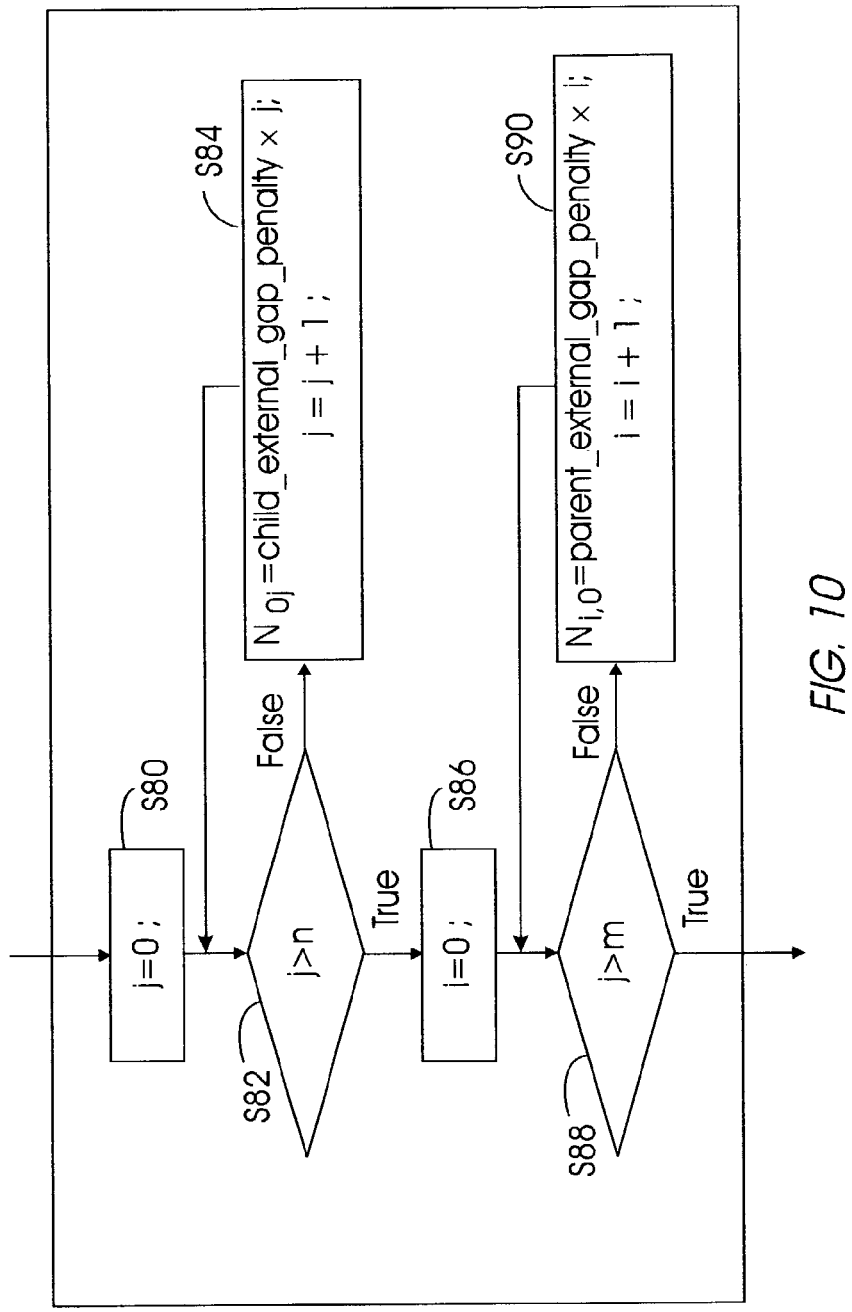
FIG. 10 shows a detailed flowchart of the initialization step shown in FIG. 9.

FIG. 10 is a flowchart showing details of the initialization at step S60 described with respect to FIG. 9. As shown in FIG. 10, variable j is first initialized to 0 at step S80. It is determined at step S82 whether j>n. If it is determined at step S82 that j>n does not hold (false), the external gap score $N_{0,j}$ of the child sequence is set for given j at step S84. Then, j is incremented by 1 and it is returned to step S82. If it is determined at step S82 that j exceeds n (false), then i is initialized to 0 at step S86 and it is determined at step S88 whether i>m. If it is determined at step S88 that i>m does not hold (false), the external gap score $N_{i,0}$ of the parent sequence is set for given i at step S90 and i is incremented by 1. Then, determination at step 88 is performed again and, if i>m (true), the initialization at step S60 ends. At this stage, the first column and row among $N_{i,j}$ elements in a table used in dynamic programming used in a certain embodiment of the present invention (hereinafter simply referred to as the table) are specified. The present invention is not limited to the technique known as dynamic programming. Any tables that are generated by any other methods may be used as long as cluster generation according to the present invention can be accomplished.

Figure 11:
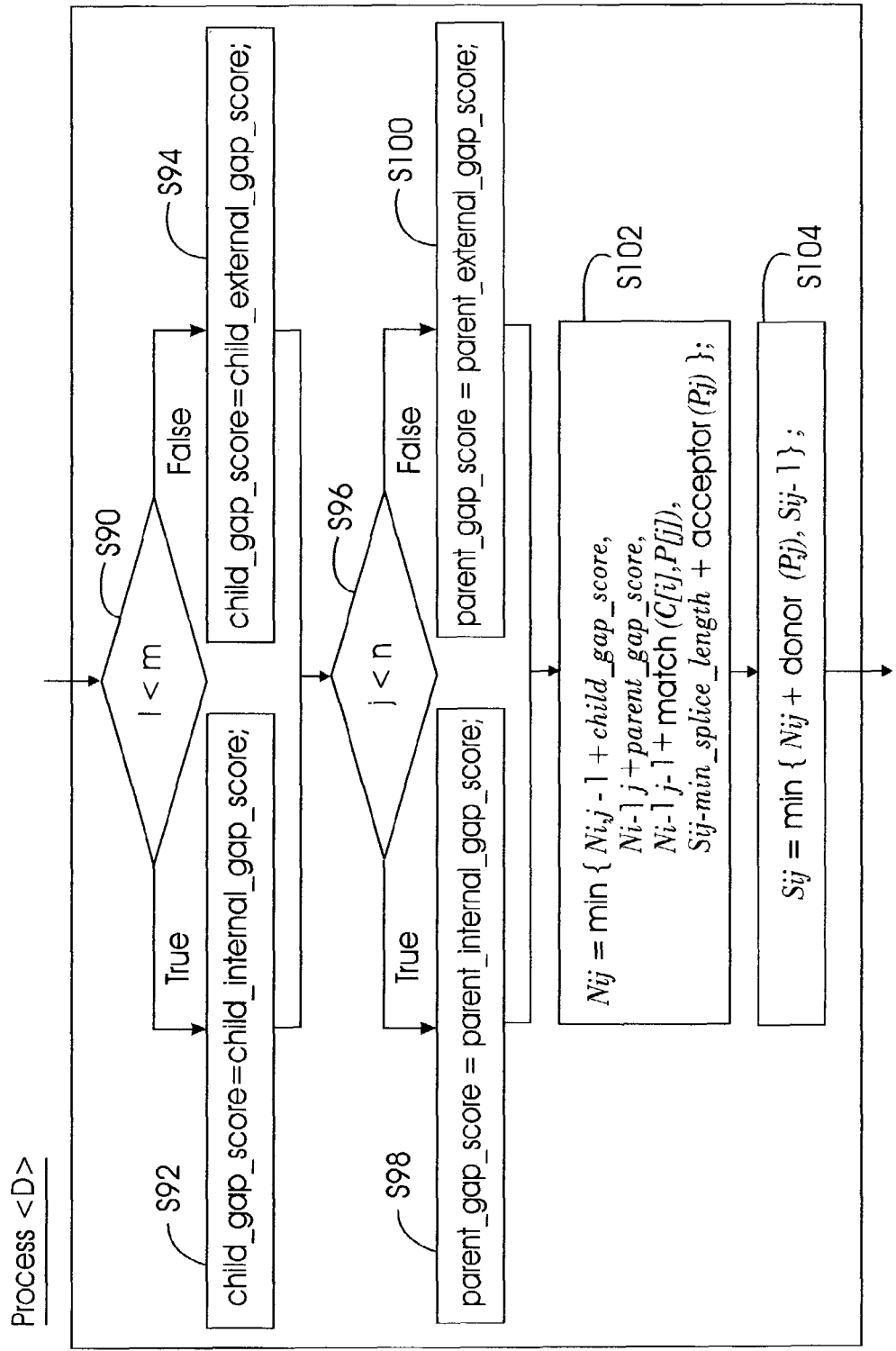
FIG. 11 shows a detailed flowchart of step S74 shown in FIG. 9.

FIG. 11 is a flowchart showing the details of the process at step S74 shown in FIG. 9. In the process at step S74 shown in FIG. 11, it is determined at step S90 whether i<m. If it is determined that i<m (true), a variable, child_gap_score is obtained as the internal gap score of the child sequence at step S92. On the other hand, if it is determined at step S90 that i<m does not hold (false), variable child_gap_score is obtained as the external gap score of the child step at step S94. Then, it is determined at step S96 whether j<n. If it is determined that j<n (true), parent_gap_score is obtained as the internal gap score of the parent sequence at step S100. On the other hand, if j<n does not hold (false) at step S96, parent_gap_score is obtained as the external gap score of the parent sequence at step S98.

Then, the elements of the table are determined at step S102 and value $S_{i,j}$ is calculated at step S104. Value $S_{i,j}$ is a score independently added to a splice site that is irrelevant to the base chain length of the child sequence. After the score of the splice site is calculated at step S104, the result is passed from step S74 in FIG. 10 to step S68 in FIG. 9, then the score value for i that is less than or equal to m is generated.

FIG. 12 shows a pseudo code for causing a computer to perform a process for generating a second cluster using the high-precision spliced alignment according to the present invention described with reference to FIGS. 9 to 11. In the pseudo code shown in FIG. 12, a parent sequence is represented by P[1 . . . n] and a child sequence is represented by C[1 . . . m] as described earlier. Function match(a, b) in this pseudo code is a matching score between base a and base b. Donor(P,i) indicates the score of the i-th donor site at P and acceptor(P,i) indicates the score of an acceptor site in that position. The pseudo code shown in FIG. 12 does not include a splice score, which is the score of a splice site. It is included in the scores of the donor site and acceptor site in the pseudo code in FIG. 12. The ultimate score, Nnm, will be obtained through the pseudo code shown in FIG. 12.

Figure 13:
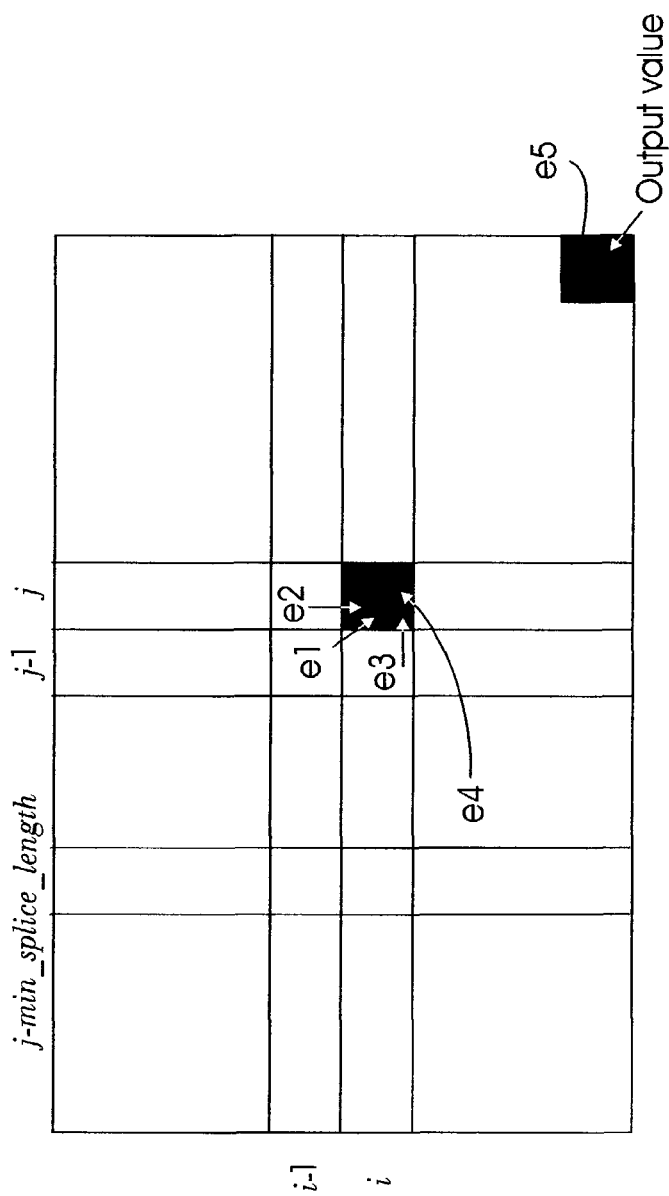
FIG. 13 schematically shows a general structure of a table according to the present invention and elements used for calculating scores.

FIG. 13 schematically shows a general structure of the above-described table and elements used for calculating scores. The table shown in FIG. 13 comprises rows of a parent base sequence and columns of a child base sequence. Elements of Ni,j in the pseudo code shown in FIG. 12 can be obtained as the smallest value among four elements: three elements e1 to e3 and e4, which is the value of $S_{i,j-1}$ described above, shown in FIG. 13. Therefore, the amount of memory required for calculations in the table shown in FIG. 13 is only that allocated for the two lines, line i–1 and line i. Accordingly, the present invention uses less hardware resources, including memory resources, thereby conserving calculation time and hardware resources. In addition, Nnm obtained as the ultimate score is indicated as e5 in FIG. 13.

Spliced alignment of a child sequence according to the present invention can be accomplished by using the score Nnm obtained for a given child sequence to provide m□r, that is, the number m of bases in the child sequence multiplied by an appropriate error rate r desired by a user and pairing child sequences providing scores less than or equal to m.quadrature.r as a spliced pair.

Any of known precise spliced alignments may be used with the present invention. For example, the method proposed by Usuka, et al. may be used.

In another embodiment of the present invention, a spliced edit distance obtained by the method of the present invention is the lower limit of the sum of the number of gaps contained and the number of mismatches contained in a parent sequence. Therefore, if no negative scores (such as a gap_score and matching score) are included in scores for parameter settings in the present invention, it is very easy to calculate the upper limit of the sum of the number of gaps and the number of mismatches contained in a parent sequence in alignment that is determined to be spliced alignment. A process may be used for excluding sequences that provides a spliced edit distance greater than the upper limit of the sum of the number of the gaps and the number of mismatches from candidates.

In another embodiment of the present invention, letting h be the spliced pair determination criterion (although h is preferably proportional to the length of a child sequence as described above, it may not be necessarily so), the upper limit of the sum of the number of gaps and the number of mismatches in a parent sequence can be expressed as follows:

$$h/\min\{parent\_external\_gap\_score, parent\_internal\_gap\_score, min\_mismatch\_sco-re\},$$

where min_mismatch_score is expressed as min.sub.a.quadrature.b {mat-ch(a,b)} and corresponds to the lowest score in base pairs that do not match. No parameters used in the present invention are required to be negative. Because it is unlikely that a gap penalty of a parent, which is the denominator, and a mismatch score are less than or equal to 0, a good upper limit of a spliced edit distance can be provided and used to reduce the number of candidates.

In yet another embodiment of the present invention, the cluster generating method of the present invention can be used with another selecting method for reducing the number of spliced pair candidates.

Figure 14:
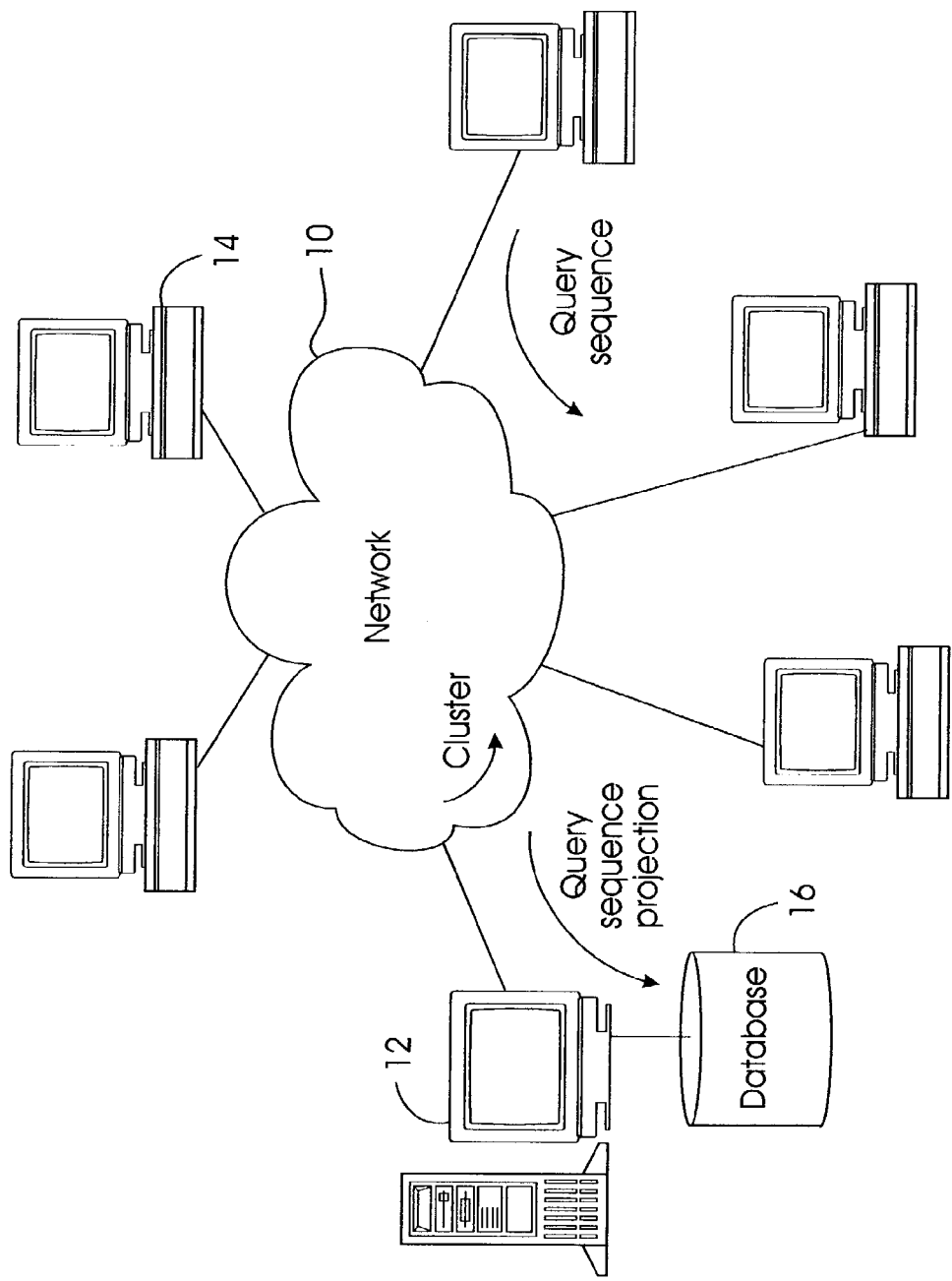
FIG. 14 shows a schematic diagram of an embodiment of a base sequence information providing system according to the present invention.

FIG. 14 shows a general view of a computer system according to the present invention. The computer system of the present invention shown in FIG. 14 comprises a server 12 connected to a network 10 such as the Internet and clients 14 for sending a query sequence to the server 12. The server 12 manages a database 16 containing base sequences. The server 12 uses a query sequence it received and projects it onto base sequences contained in the database 16 to generate the first cluster through global filtering according to the present invention.

In a certain embodiment described herein, a base sequence may be cDNA and a query sequence may be mRNA. However, the present invention can be applied to any base sequences derived from various organisms, including viruses and bacteria, besides eucaryote, to which a splice site and a splice length according to the present invention can be applied. The first cluster is used to perform high-precision spliced alignment to generate a second cluster and the second cluster is provided to the user.

Figure 15:
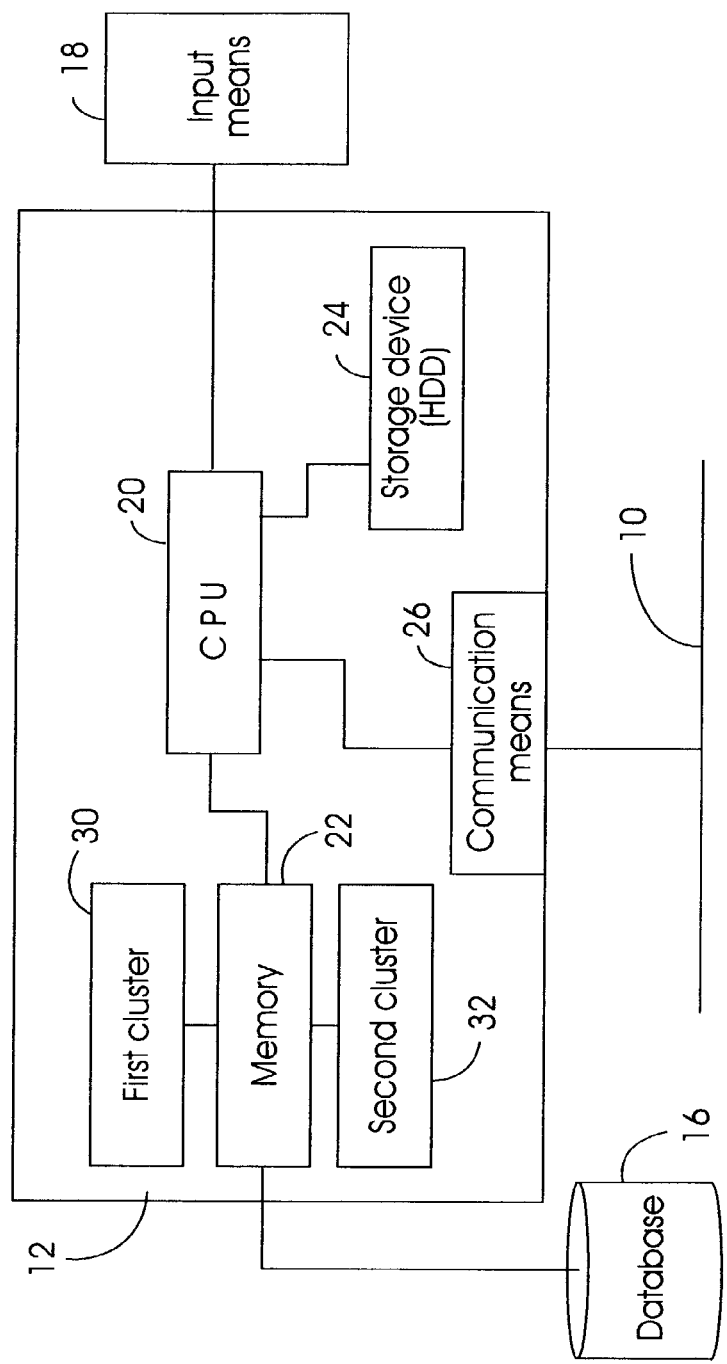
FIG. 15 shows a block diagram of a configuration of a server performing the cluster generation according to the present invention.

FIG. 15 shows a block diagram of a server 12 programmed and configured for performing the cluster generating method and clustering method according to the present invention. As shown in FIG. 15, the server 12 manages a database 16 containing base sequences such as cDNAs and can store a newly found base sequence in the database 16 when it is input from input means 18 such as a keyboard. The server 12 comprises a central processing unit (CPU) 20 for performing a program of the present invention and a memory 22 for holding the program, an active table, generated clusters of base sequences, and other data. The server 12 also manages a storage device 24 including a storage medium, such as a hard disk, on which the program of the present invention is recorded. The server 12 can read and execute the program of the present invention from the storage device 24 in response to a request from a user.

The server 12 of the present invention further comprises communication means 26 including a network interface card (NIC), modem, and DSU and can communicate with clients, which are not shown, over a network 10 using a medium such as Ethernet®, a public telephone line, ISDN, optical communication line, and ADSL that interconnects them.

When the program including the cluster generating method of the present invention is activated by the user, the server 12 of the present invention projects a query sequence, which query sequence is input by the user or obtained through the network 10, onto base sequences contained in the base database 16 to generate a first cluster 30.

The server uses the generated first cluster to perform spliced alignment to generate a second cluster 32 consisting of high-precision spliced pairs. The second cluster 32 may be of any format. For example, it may be a table listing base sequences constituting spliced pairs for a query sequence. The second cluster 32 thus generated is sent to a client computer, not shown, over the network 10.

The program for causing the cluster generating method according to the present invention to be performed may be written in any of various programming languages, such as C, and C++, Java®. Codes describing the program of the present invention may be held in a computer-readable recording medium such as magnetic tape, a flexible disk, hard disk, compact disk, magneto-optical disk, and a digital versatile disk (DVD).

ILLUSTRATIVE EXAMPLES

The present invention will be described below with respect to specific embodiments. However, the present invention is not limited to the examples described below, which are purely illustrative and exemplary, and not intended to be limiting.

Example 1

In a Example 1 of the present invention, experiments have been conducted for finding all spliced pairs from FANTOM1.10 library (Kawai et al., Functional annotation of a full-length mouse cDNA collection, Nature 409:685-690 (2001)), which contains cDNA of mice as base sequences. In the experiments, all the combinations were calculated that provide a score less than or equal to 5% of the length of a child sequence in spliced alignment, which will be described below. Conditions used in this example will be shown in Table 1 below.

TABLE 1

| | |
|---|---|
| Mismatch score: | 1.0 |
| Match score: | 0.0 |
| Score of gaps in parent sequence: | 1.0 |
| Score of gaps in child sequence | |
| Internal gaps in sequence: | 1.0 |
| External gaps in sequence: | 0.0 |
| Shortest length of splice site: | 50 |
| Score per splice site: | 2.0 (regardless of length) |
| Donor other than GT: | +1.0 |
| Acceptor other than AG: | +1.0 |

Spliced alignment was performed on sequences in cDNA library under the conditions provided above. The 78th base sequence (accession number AK002309) in FANTOM1.10 library was used as a query sequence. As a parent sequence, the 20621st base sequence in FANTOM1.10 library that was found to be a spliced pair from other experiments was used. FIGS. 16 and 17 show query sequences and parent sequences used in the present invention. A bar "-" in the alignments shown in FIGS. 16 and 17 indicates a gap in the alignment and "=" indicates a splice site. Parent sequences are indicated in the upper rows and query sequences are indicated in the lower rows in the alignment shown in FIGS. 16 and 17.

According to the present invention, the score, 12.0, of the alignment under the above-described conditions was obtained. This score is less than or equal to 5% of the length (1162) of the query sequence and therefore shows that the query sequence and the parent sequence have splicing relation with each other. The donor and acceptor sites at the splice sites of query sequence and parent sequence were normal GT-AG pair. This embodiment, which is a typical example of the present invention, shows that they were properly listed as a spliced pair as confirmed by the present invention.

Example 2

The same parent sequence was used to perform spliced alignment of query sequences with parent sequences. Since the cDNA library contains 21,706 sequences, the number of possible pairs is 21,706×21,705=441–76,700 (there is the distinction between parent and child sequences). A filter using hashing was applied to these pairs to find out pairs having a common partial sequence to narrow down the number of pairs to 288,380. Computation time required for this narrowing down using Workstation RS-6000 (from International Business Machines Corporation) containing RS64III processor (450 MHz) from International Business Machines Corporation was 205 seconds.

The number of candidate base sequence pairs was reduced from 288,380 to 37,812 to generate a first cluster according to the present invention. This calculation took 2,765 seconds (approximately 44 minutes). The first cluster containing 37,812 base sequence pairs obtained was used to perform spliced alignment with the query sequences. It took 79,399 seconds (approximately 22 hours) for spliced alignment to be obtained. As the result of this calculation, 5,140 pairs having splicing relation with each other were listed. Based on this result, it is possible to classify the cDNA library into 16,532 groups corresponding to different regions of eucaryote genome DNA.

Comparative Example

As a comparative example, the same set of conditions, parent sequences, and query sequences as those in the Example 2 was used to perform spliced alignment of the query sequences with the parent sequences. The method by Usuka et al. was used to directly apply the spliced alignment to 288,380 base sequence pairs obtained through hashing. It took up to approximately 200 hours of calculation to obtain the same result as that of Example 2. This demonstrates that the calculation time is significantly reduced by base sequence clustering according to the present invention.

Thus, the present invention provides a cluster generating system, a method for enabling base sequence clustering, a program for causing the method to be performed, and a computer-readable storage medium containing the program that can associate base sequence contained in a database such as a cDNA database with base sequences that are likely to be generated through splicing from the cDNAs to perform fast clustering, thereby conserving calculation time and hardware resources. The present invention can also provide a cluster generating system, a method for enabling base sequence clustering, a program for causing the method to be performed, and a computer-readable storage medium containing the program that enables a user to generate clusters in a limited time period with relaxing hardware resource constraints.

Furthermore, the present invention can provide a system for presenting base sequence information that can efficiently provide base sequence information relating to spliced pairs.

While the present invention has been described with respect to specific embodiments, the present invention is not limited to the specific embodiments described herein. The present invention can be applied to base sequences of any organisms that are cut with before-and-after-cut relation being maintained and have approximation between them. Splice sites in the present invention are not limited to GT-AG pairs. The present invention can be applied to any known pairs or pairs that provide functions equivalent to those of known pairs.

I claim:

1. A system for providing information about a cluster of child spliced sequences obtained from a parent base sequence comprising a server for receiving a query sequence and a database containing base sequences, wherein said server comprises:
   a subsystem for recording a plurality of spliced sequences, wherein each spliced sequence is a query sequence;
   a subsystem for comparing a spliced edit distance between each query sequence and the parent base sequence read from a database with a predetermined maximum acceptable value;
   a subsystem for selecting spliced base sequences of which the spliced edit distance between each query sequence and the parent base sequence is not more than said maximum acceptable value to generate a first cluster of child spliced sequences and recording said first cluster in a storage subsystem;
   a subsystem for generating a second cluster of child spliced sequences from said first cluster and storing said second cluster; and
   a subsystem for sending said second cluster over a network, wherein the second cluster of child spliced sequences comprises spliced pairs between each query sequence and the base sequence with a defined splice length for the base sequence and applying spliced alignment between each query sequence and the first cluster as aligned with the base sequence, wherein the degree of spliced alignment between each query sequence and the base sequence is determined by the number of spliced pairs of the second cluster at the defined splice length.

2. The system of claim 1, wherein said spliced edit distance comparing subsystem comprises a difference counter decrementing from said maximum acceptable value when a base in said base sequence matches a base in each query sequence.

3. The system of claim 1, wherein said network is Internet based.

4. The system of claim 1, wherein said network is a local area network (LAN).

5. The system of claim 3, further comprising:
   a subsystem for assigning a score to the base sequence based upon the degree of spliced alignment between the query sequence and the base sequence as determined by the number of spliced pairs of the second cluster;
   a subsystem for generating a table by repeated generation of said score to correspond to the splice length; and
   a subsystem for using contents of said table to determine a score for said base sequence with respect to each query sequence.

6. The system of claim 1, wherein said splice length is the number of bases within the range from 20 to 60.

7. The system of claim 1, wherein said parent base sequence from the database comprises a DNA sequence of a eukaryote.

8. The system of claim 1, wherein said query sequence comprises DNA spliced sequences.

9. The system of claim 1, wherein said query sequence comprises cDNA spliced sequences obtained through reverse transcription from mRNA expressed in said eukaryote.

10. The system of claim 1, wherein said query sequence comprises cDNA spliced sequences obtained through reverse transcription from mRNA expressed in base sequences of said mRNA.

11. The system of claim 1, wherein said second cluster is stored in computer memory.

12. The system of claim 1, wherein said second cluster is stored in a computer hard disk.

13. The system of claim 1, wherein said stored second cluster is displayed on a display screen.

14. The system of claim 1, wherein said server is connected to the network and said query sequence is received by said server over said network.

15. The system of claim 14, wherein said network is Internet based.

16. The system of claim 14, wherein said network is a local area network (LAN).

17. The system of claim 14, wherein said server further comprises communication means for communicating with clients over the network.

18. The system of claim 17, wherein said communications means are selected from the group consisting of a network interface card (NIC), a modem, and a data service unit (DSU).

19. The system of claim 17, wherein said clients are connected to the server over the network with a medium selected from the group consisting of an Ethernet® connection, a public telephone line, an integrated service digital network (ISDN), an optical communication line, and an asymmetric digital subscriber line (ADSL).

* * * * *

SEQUENCE LISTING

```
<160> NUMBER OF SEQ ID NOS: 5

<210> SEQ ID NO 1
<211> LENGTH: 1162
<212> TYPE: DNA
<213> ORGANISM: Mus musculus
<220> FEATURE:
<221> NAME/KEY: misc_feature
<222> LOCATION: (1)..(1162)
<300> PUBLICATION INFORMATION:
<308> DATABASE ACCESSION NUMBER: AK002309
<309> DATABASE ENTRY DATE: 2002-12-05
<313> RELEVANT RESIDUES IN SEQ ID NO: (1)..(1162)

<400> SEQUENCE: 1
ggctcttgaa aaaacgctgg agctgaggat ttcatctcgg atttcatcta acattatggg      60
ccgcaagaaa gttgctcgcg gatccaggaa agagagcggt cgtgttcggc gaccctctgg    120
ccgctctctg gatgctttcg ctgaagaggt gggcgctgcg ctgcgtgcat ccgtgcagcc    180
cgaggaggcc gaggaccagg gcggcccggg ccctgcggcg ctgccttgtg ccttggctat    240
gtgggagctt ggtcactgcg accccaagcg ctgcacgggc cgcaaactgg cccgtctggg    300
tctggtgcgc tgcctgcgcc tgagccaaag gtttggcggt ctggtgctca gcccagtagg    360
cactgagtac gtgtctccgg cagacagaca gctggtggca cagtcagggg tcgcagtcat    420
agactgctcc tgggccaaac tggacgacac acccctttcag aagatgcgag ggagccactt    480
gcggctcctg ccttacctcg tagctgccaa ccctgtaaac tatggccggc cctgcaaact    540
ttcctgtgtg aagctttcg ctgctgcctt ctgcatcgta ggcttttcag accttgctgt    600
cattttgctt cggaagttta agtggggcaa gggcttcctg gacctgaacc gggagctcct    660
ggataagtac gcagcttgcc gtggcccgga ggaggtgttg caggctgaac aggggtactt    720
ggctagcacc agggacacgc ctgaagagga catcgatccc tttgacgtgg actcagggcg    780
ggagtttgag aatctcaaca ggcccgtggc cagcacccgg ctacctgagg acatggatga    840
cactgatggg tctgaggagc acagtgaaga ttctgaggag gacagtgatg agtgtgagga    900
accaggacct ggtgctaatg gaggagacag caactactct ggagctgaag agaccccaga    960
acaagaggct caagccagag actccactga aatttggaaa gggatcaaga aacgacagag   1020
agactgaagg tcacaaacat attattgaag ctggtgtgca ttattcagaa gtggcagtag   1080
gacctgggga tggacgggcc tgctgggaca accttgttta gtgtcctgcc ttagtgctct   1140
caataaaacc aagggacccc ct                                              1162

<210> SEQ ID NO 2
<211> LENGTH: 1937
<212> TYPE: DNA
<213> ORGANISM: Mus musculus
<220> FEATURE:
<221> NAME/KEY: misc_feature
<222> LOCATION: (1)..(1937)
<300> PUBLICATION INFORMATION:
<308> DATABASE ACCESSION NUMBER: AK003675
<309> DATABASE ENTRY DATE: 2002-12-05
<313> RELEVANT RESIDUES IN SEQ ID NO: (1)..(1937)
```

<400> SEQUENCE: 2

```
ggctcttgaa caaacgctgg agctgaggat ttcatctcgg atttcatcta acattatggg      60
ccgcaagaaa gttgctcgcg gatccaggaa agagagcggt cgtgttcggc gaccctctgg    120
ccgctctctg gatgctttcg ctgaagaggg gggcgctgcg ctgcgtggtg agtttggagc    180
agtcggagca gcgggtcggg cctgggagca ggcgctgagg acccggcctt ctctctctcc    240
ttgtagcatc cgtgcagccc gaggaggccg aggaccaggg cggcccgggc cctgcggcgc    300
tgccttgtgc cttggctatg tgggagcttg gtcactgcga ccccaagcgc tgcacgggcc    360
gcaaactggc ccgtctgggt ctggtgcgct gcctgcgcct gagccaaagg tttggcggtc    420
tggtgctcag cccagtaggc actgagtacg tgtctccggc agacaggtag acaccagagg    480
cctggggatc ggggaggggt cggagagggg ttggaatgcc cttcccacca tcttgtcttt    540
gttaaactgc cctgtatcag gagtatcatt ttcttcaagc cttgcttatt ggtcttggat    600
gtccacatct ttcatatgag cagagttgta tttaatttga ccctttttcat agagcagggc   660
tatagtgtag aaagcctagg agaaacattt gttgtgtaaa gtaaacactg tccagctacc    720
ctcaactgct tcctgaaggg ttcttttctac tattgcaata aaccataact tcgaaatagc    780
agagtgatct ctcatctgta gtgaagccag tctccaagga tgtgccttat ttggggccct   840
agaacctacc ctacactctc tgacagacag ctggtggcac agtcaggggt cgcagtcata    900
gactgctcct gggccaaact ggacgacaca ccctttcaga agatgcgagg gagccacttg    960
cggctcctgc cttacctcgt agctgccaac cctgtaaact atggccggcc ctgcaaactt   1020
tcctgtgtgg aagctttcgc tgctgccttc tgcatcgtag gcttttcaga ccttgctgtc   1080
attttgcttc ggaagtttaa gtggggcaag ggcttcctgg acctgaaccg ggagctcctg   1140
gataagtacg cagcttgccg tggcccggag gaggtgttgc aggctgaaca ggggtacttg   1200
gctagcacca gggacacgcc tgaagaggac atcggtgagt cctggtgttg gctgggagcc   1260
ccagagaagc aatcaagtcc ctccagggcc ttaggagcct agagcctgaa aatcacttag   1320
aagtccccctt cctctcttct tctttctttc tttctttttt ttttgggggt gggggtgggg   1380
gtggggagag ggtttctctg tgtagtcctg gctgtcctgg aactcacttt gtagaccagg   1440
ctggcctcaa actcagaaat ccgcctgcct ctgcctcccg agtgctggga ttaaaggtgt   1500
gcgccaccac gccctctctt tctgtgttca gatcccttgg acgtggactc agtgcgggag   1560
tttgtgaatc tcaacaggcc cgtggccagc acccggctac ctgaggacat ggatgacact   1620
gatgggtctg aggagcacag tgaagattct gaggaggaca gtgatgagtg tgaggaacca   1680
ggacctggtg ctaatggagg agacagcaac tactctggag ctgaagagac cccagaacaa   1740
gaggctcaag ccagagactc cactgaaatt tggaaaggga tcaagaaacg acagagagac   1800
tgaaggtcac aaacatatta ttgaagctgg tgtgcattat tcagaagtgg cagtaggacc   1860
tggggatgga cgggcctgct gggacaacct tgtttagtgt cctgccttag tgctctcaat   1920
aaaaccaagg agacccc                                                   1937
```

<210> SEQ ID NO 3
<211> LENGTH: 40
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(40)

```
<400> SEQUENCE: 3
ggctcttgaa caaacgctgg agctgaggat tcatctcgga                                40

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)

<400> SEQUENCE: 4
gctgagaaga ggtttcatct                                                      20

<210> SEQ ID NO 5
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(10)

<400> SEQUENCE: 5
cgcgcatgaa                                                                 10
```